(12) United States Patent
Ohguri

(10) Patent No.: US 12,150,805 B2
(45) Date of Patent: Nov. 26, 2024

(54) RADIOGRAPHIC APPARATUS, METHOD OF CONTROLLING THE SAME, RADIOGRAPHIC SYSTEM, AND STORAGE MEDIUM

(71) Applicant: CANON KABUSHIKI KAISHA, Tokyo (JP)

(72) Inventor: Hirokazu Ohguri, Chiba (JP)

(73) Assignee: Canon Kabushiki Kaisha, Tokyo (JP)

(*) Notice: Subject to any disclaimer, the term of this patent is extended or adjusted under 35 U.S.C. 154(b) by 356 days.

(21) Appl. No.: 17/545,913

(22) Filed: Dec. 8, 2021

(65) Prior Publication Data

US 2022/0183647 A1 Jun. 16, 2022

(30) Foreign Application Priority Data

Dec. 16, 2020 (JP) ................................ 2020-208142

(51) Int. Cl.
*A61B 6/00* (2024.01)
(52) U.S. Cl.
CPC . *A61B 6/54* (2013.01); *A61B 6/56* (2013.01)
(58) Field of Classification Search
CPC ........... A61B 6/56; A61B 6/54; A61B 6/4233; A61B 6/463; A61B 6/5258; A61B 6/582; A61B 6/44; A61B 6/548; A61B 6/566; A61B 6/4283; A61B 6/542; A61B 6/487; A61B 6/46; A61B 6/465; A61B 6/5205; A61B 6/4208; A61B 6/461; A61B 6/5241; A61B 6/00; A61B 6/467; A61B 6/5294; A61B 6/468; A61B 6/4266; A61B 6/488;

(Continued)

(56) References Cited

U.S. PATENT DOCUMENTS

2014/0254760 A1* 9/2014 Hiroike ................ A61B 6/4233
378/62
2015/0378030 A1* 12/2015 Tamura .................... H04N 5/32
378/98.2

(Continued)

FOREIGN PATENT DOCUMENTS

JP 2002165142 A 6/2002
JP 2002272720 A 9/2002

(Continued)

*Primary Examiner* — Irakli Kiknadze
(74) *Attorney, Agent, or Firm* — Canon U.S.A., Inc. IP Division

(57) ABSTRACT

A mechanism to select an optimum standby state canceling method in terms of power consumption. A radiographic apparatus is configured to capture a radiographic image based on an incident radiation and operates in any of a plurality of standby states different in power consumption. Each of the standby states is less in power consumption than a radiography-enabled state where the radiographic apparatus is enabled to capture the radiographic image. A selection unit selects a standby state from the plurality of standby states so that a transition time is shorter than an irradiation preparation time. The transition time is a time necessary for the radiographic apparatus to make a transition from the standby state to the radiography-enabled state. The irradiation preparation time is a time necessary for a radiation generation apparatus configured to generate a radiation to prepare irradiation of the radiation after a radiation irradiation preparation request is received.

13 Claims, 12 Drawing Sheets

(58) Field of Classification Search
CPC ....... A61B 6/464; A61B 6/563; A61B 6/4494;
A61B 6/545; G01N 23/04; G01N
2223/303; G01N 2223/306; G01N 23/06;
G01N 2223/40; G01N 2223/04; G01T
1/17; G01T 1/175; G01T 7/00; G01T
1/2006; G01T 1/247; H04N 25/75; H04N
25/709; H04N 23/30; H02J 50/80; H02J
50/10; H02J 7/00; H02J 50/90
USPC .................................................. 378/62, 101
See application file for complete search history.

(56) References Cited

U.S. PATENT DOCUMENTS

| | | | |
|---|---|---|---|
| 2016/0029991 A1* | 2/2016 | Tajima | A61B 6/467 |
| | | | 250/336.1 |
| 2019/0282196 A1 | 9/2019 | Tezuka | |
| 2020/0120783 A1* | 4/2020 | Kuwata | A61B 6/542 |

FOREIGN PATENT DOCUMENTS

| | | | |
|---|---|---|---|
| JP | 2006208319 A | 8/2006 | |
| JP | 2008073121 A | 4/2008 | |
| JP | 2014171523 A | 9/2014 | |

* cited by examiner

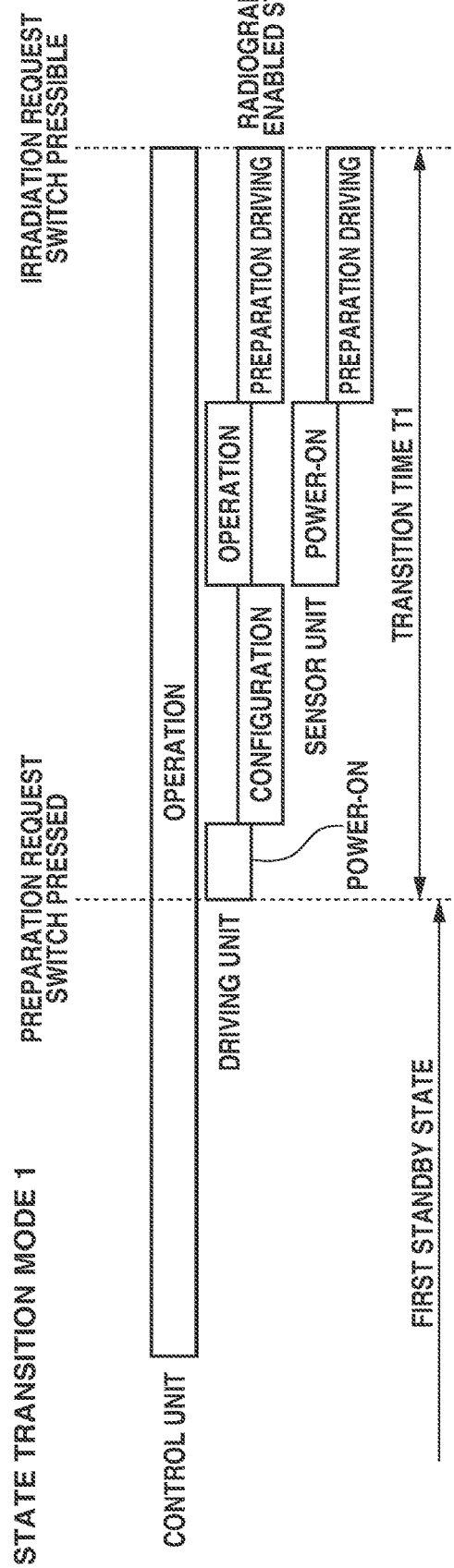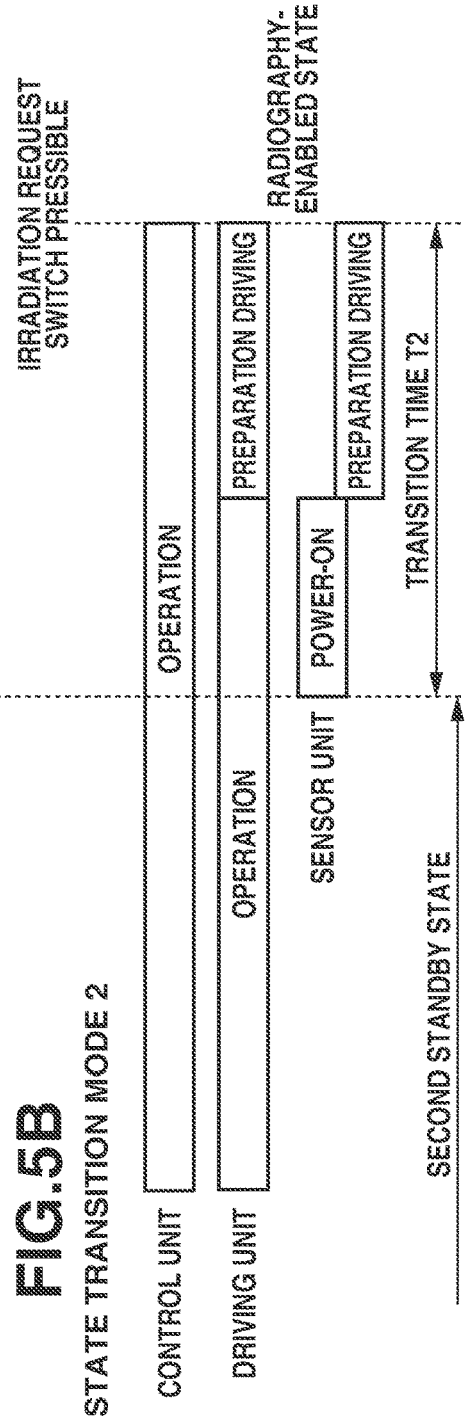

FIG.6

|  | POWER CONSUMPTION IN STANDBY STATE | TRANSITION TIME TO RADIOGRAPHY-ENABLED STATE |
|---|---|---|
| STATE TRANSITION MODE 1 | SMALL | LONG |
| STATE TRANSITION MODE 2 | MIDDLE | MIDDLE |
| STATE TRANSITION MODE 3 | LARGE | SHORT (NONE) |

FIG.11

| RADIATION GENERATION APPARATUS | STATE TRANSITION MODE |
|---|---|
| GENERAL RADIOGRAPHY ROOM A | STATE TRANSITION MODE 1 |
| GENERAL RADIOGRAPHY ROOM B | STATE TRANSITION MODE 2 |
| INSTRUMENT CARRIAGE | STATE TRANSITION MODE 3 |

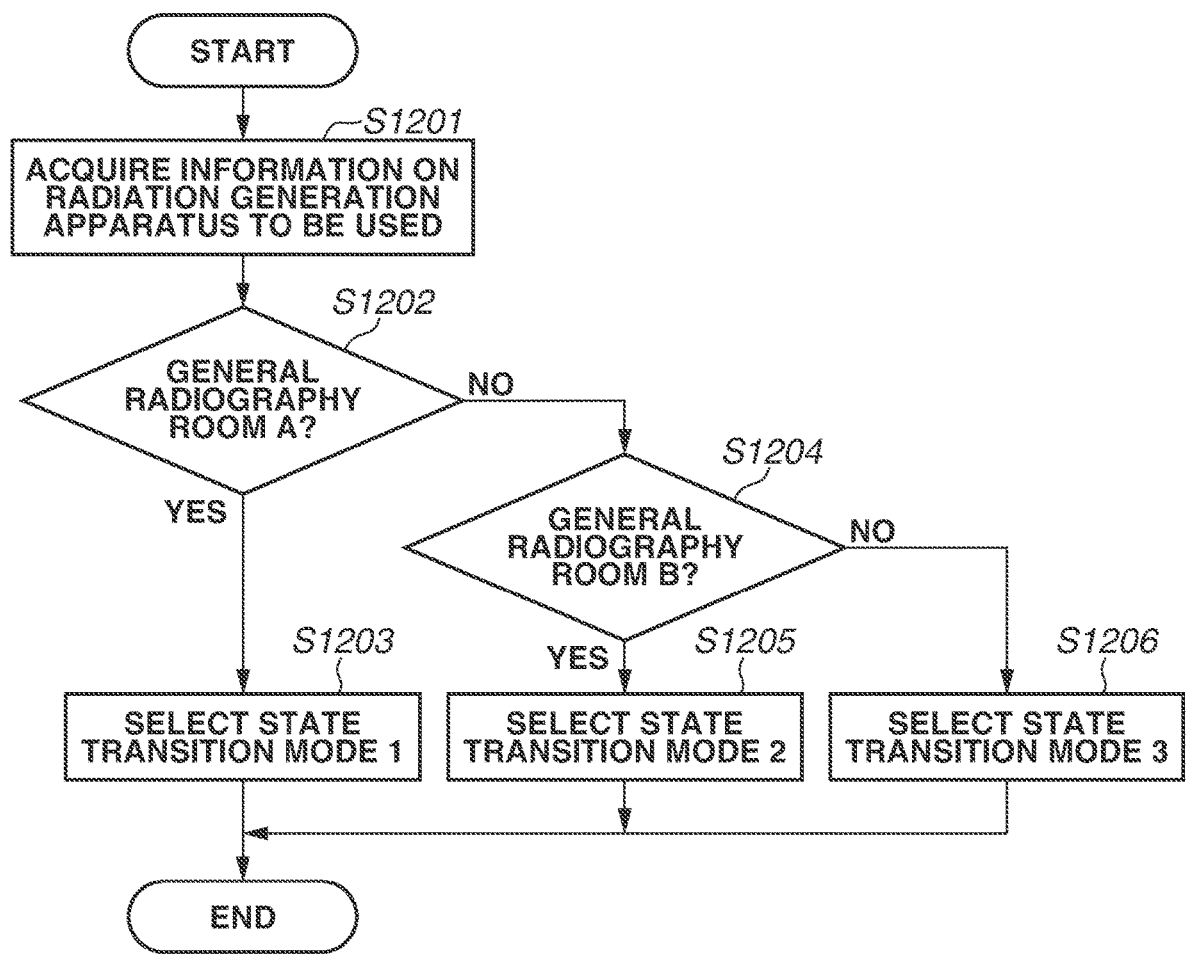

RADIOGRAPHIC APPARATUS, METHOD OF CONTROLLING THE SAME, RADIOGRAPHIC SYSTEM, AND STORAGE MEDIUM

CROSS REFERENCE TO RELATED APPLICATION

This application claims the benefit of Japanese Patent Application No. 2020-208142, filed Dec. 16, 2020, which is hereby incorporated by reference herein in its entirety.

BACKGROUND

Field of the Disclosure

The present disclosure relates to a radiographic apparatus performing radiography, a method of controlling the radiographic apparatus, a radiographic system, and a storage medium storing a program for causing a computer to function as the radiographic apparatus.

Description of the Related Art

In recent years, digitalization of a radiographic system has progressed with popularization of a radiographic apparatus that generates a digital radiographic image based on an incident radiation. The digitalization of the radiographic system enables checking of an image immediately after radiography, and significantly improves a workflow as compared with an existing radiography method using a film and a computed radiography (CR) apparatus.

Further, development of a wireless radiographic apparatus has made handling of the radiographic apparatus easier. Such a wireless radiographic apparatus is operated by a battery. Thus, the number of images that can be captured per charging leads to usability. At this time, to increase the number of images that can be captured, power saving of the radiographic apparatus is necessary. Further, the digital radiographic apparatus needs a predetermined waiting time because the digital radiographic apparatus makes a transition to a radiography-enabled state after canceling a standby state less in power consumption than the radiography-enabled state. The shorter the time to radiography, the better for an operator and a patient. Thus, Japanese Patent Application Laid-Open No. 2002-165142 discusses a plurality of standby state canceling methods. Further, Japanese Patent Application Laid-Open No. 2002-272720 discusses a method of canceling the standby state in response to input of a radiography order.

As described above, Japanese Patent Application Laid-Open No. 2002-165142 discusses the plurality of standby state canceling methods; however, there is an issue that, for example, a standby state canceling method large in power consumption is selected even though the waiting time until radiation irradiation is the same.

Further, Japanese Patent Application Laid-Open No. 2002-272720 discusses the method of canceling the standby state in response to input of the radiography order; however, there is an issue that, when a time from the input of the radiography order to radiography is long, power consumption is increased.

SUMMARY

The present disclosure is directed to a mechanism that enables, in a case where a radiographic apparatus has a plurality of standby state canceling methods, selection of an optimum standby state canceling method in terms of power consumption.

According to an aspect of the present invention, a radiographic apparatus configured to capture a radiographic image based on an incident radiation, the radiographic apparatus operating in any of a plurality of standby states different in power consumption, each of the standby states being less in power consumption than a radiography-enabled state where the radiographic apparatus is enabled to capture the radiographic image, includes a selection unit configured to select a standby state from the plurality of standby states so that a transition time is shorter than an irradiation preparation time, the transition time being a time necessary for the radiographic apparatus to make a transition from the standby state to the radiography-enabled state, the irradiation preparation time being a time necessary for a radiation generation apparatus configured to generate a radiation to prepare irradiation of the radiation after a radiation irradiation preparation request is received.

Further features of the present invention will become apparent from the following description of exemplary embodiments with reference to the attached drawings.

BRIEF DESCRIPTION OF THE DRAWINGS

FIGS. 5A and 5B are conceptual diagrams illustrating transition operation of one of the radiographic apparatuses.

FIG. 6 is a diagram illustrating a relationship between each state transition mode and power consumption in a standby state.

FIG. 11 is a diagram illustrating an association relationship between the state transition modes and the radiation generation apparatuses.

FIG. 12 is a flowchart illustrating an example of a processing procedure according to a third exemplary embodiment.

DESCRIPTION OF THE EMBODIMENTS

Some exemplary embodiments of the present invention are described below with reference to the drawings. The exemplary embodiments of the present disclosure described below do not limit the invention set forth in the claims, and not all the combinations of features described in the exemplary embodiments of the present invention are always essential for solving means of the present invention. Further, in the exemplary embodiments of the present invention described below, an X-ray is suitable as a radiation; however, the present invention is not limited thereto, and other radiations such as an α-ray, a β-ray, and a γ-ray are also applicable to the present invention.

First, a first exemplary embodiment of the present invention is described.

Figure 1:
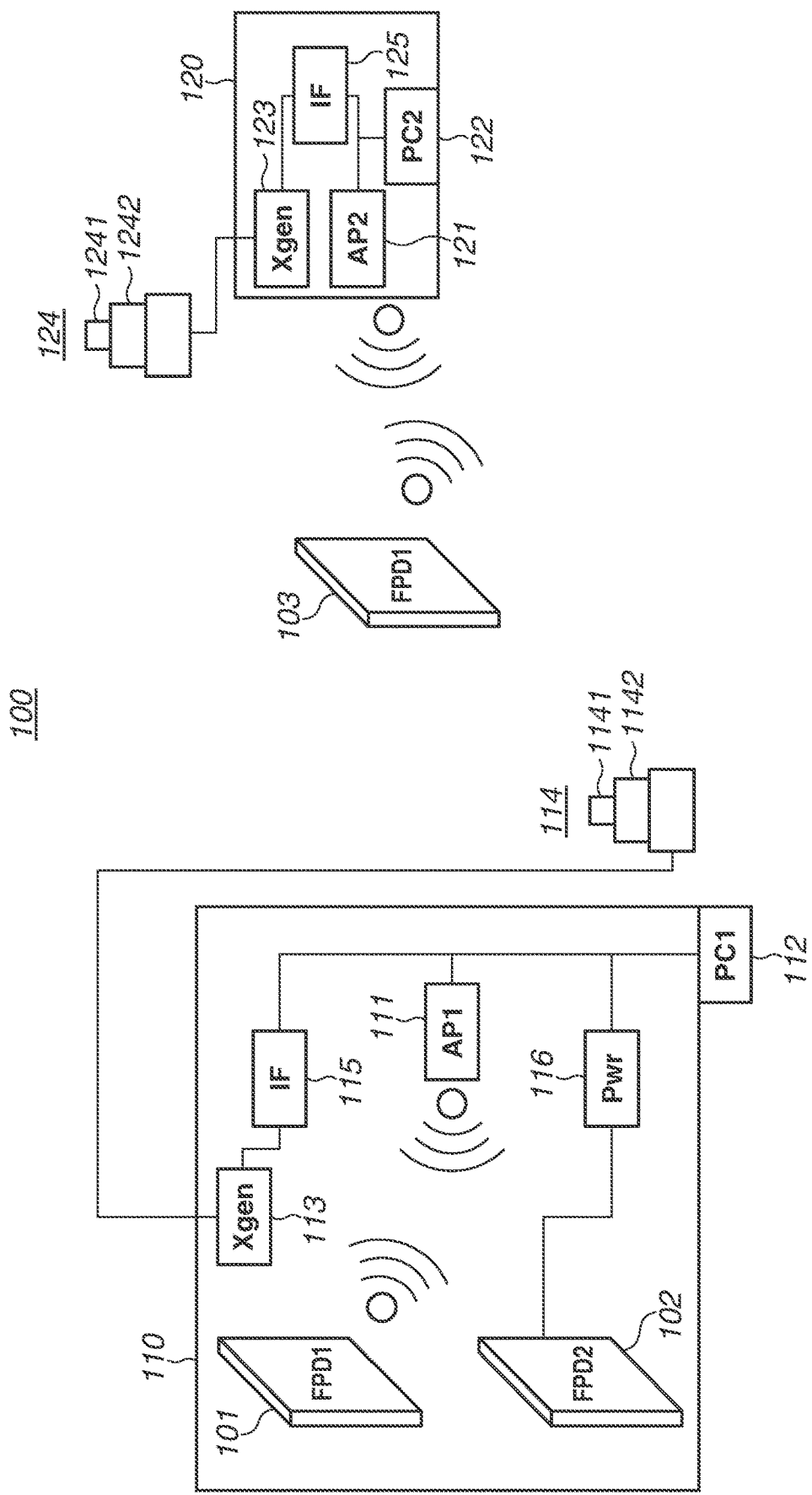
FIG. 1 is a diagram schematically illustrating an example of a configuration of a radiographic system.

FIG. 1 is a diagram schematically illustrating an example of a configuration of a radiographic system 100 according to the first exemplary embodiment of the present invention. The radiographic system 100 according to the present exemplary embodiment includes a configuration on a side of a radiography room 110 and a configuration on a side of an instrument carriage 120.

A radiographic apparatus 101 and a radiographic apparatus 102 are disposed on the side of the radiography room 110 (more specifically, inside the radiography room 110). A radiographic apparatus 103 is disposed on the side of the instrument carriage 120. For example, the radiographic apparatus 101 can be moved and disposed also on the side of the instrument carriage 120. The radiographic apparatuses 101 to 103 can operate by respective batteries or by an external power supply.

On the side of the radiography room 110, a wireless access point 111 (illustrated as AP1 in FIG. 1) and a console 112 (illustrated as PC1 in FIG. 1) that controls the radiographic apparatuses 101 and 102 are disposed in addition to the radiographic apparatuses 101 and 102. Further, on the side of the radiography room 110, a radiation generation apparatus 113 (illustrated as Xgen in FIG. 1) and a radiation switch 114 are disposed. Further, on the side of the radiography room 110, a repeater 115 (illustrated as IF in FIG. 1) that adjusts timings of the radiographic apparatuses 101 and 102 and the radiation generation apparatus 113, and a power supply apparatus 116 (illustrated as Pwr in FIG. 1) are disposed. The radiation switch 114 includes a preparation request switch 1141 that issues an instruction for a preparation start request of radiation irradiation to the radiation generation apparatus 113, and an irradiation request switch 1142 that issues an instruction for a radiation irradiation request. The preparation request switch 1141 and the irradiation request switch 1142 constitute a two-step switch, and the preparation request switch 1141 is always pressed before the irradiation request switch 1142. The power supply apparatus 116 is an apparatus that supplies power to the radiographic apparatus (e.g., radiographic apparatus 102 in FIG. 1). However, the power supply apparatus 116 not only supplies power but also includes an interface for wired communication and can relay communication between the radiographic apparatus and each of the communication apparatuses. The radiographic apparatus 101 operates by the battery, and performs wireless communication with the wireless access point 111 to transmit a radiographic image to the console 112. The radiographic apparatus 102 is connected to the power supply apparatus 116, and operates by an external power supply to perform wired communication.

On the side of the instrument carriage 120, a wireless access point 121 (illustrated as AP2 in FIG. 1) and a console 122 (illustrated as PC2 in FIG. 1) that controls the radiographic apparatus 103 are disposed in addition to the radiographic apparatus 103. Further, on the side of the instrument carriage 120, a radiation generation apparatus 123 (illustrated as Xgen in FIG. 1), a radiation switch 124, and a repeater 125 (illustrated as IF in FIG. 1) that adjusts timings of the radiographic apparatus 103 and the radiation generation apparatus 123 are disposed. The radiation switch 124 includes a preparation request switch 1241 that issues an instruction for a preparation start request of radiation irradiation to the radiation generation apparatus 123, and an irradiation request switch 1242 that issues an instruction for a radiation irradiation request. The preparation request switch 1241 and the irradiation request switch 1242 constitute a two-step switch, as with the preparation request switch 1141 and the irradiation request switch 1142. In a case where the radiographic apparatus 103 is used with the instrument carriage 120, the radiographic apparatus 103 performs wireless communication with the wireless access point 121 to transmit a radiographic image to the console 122.

Each of the radiographic apparatuses 101 to 103 can switch between wireless and wired communication connections in the radiography room 110 or the instrument carriage 120.

Figure 2:
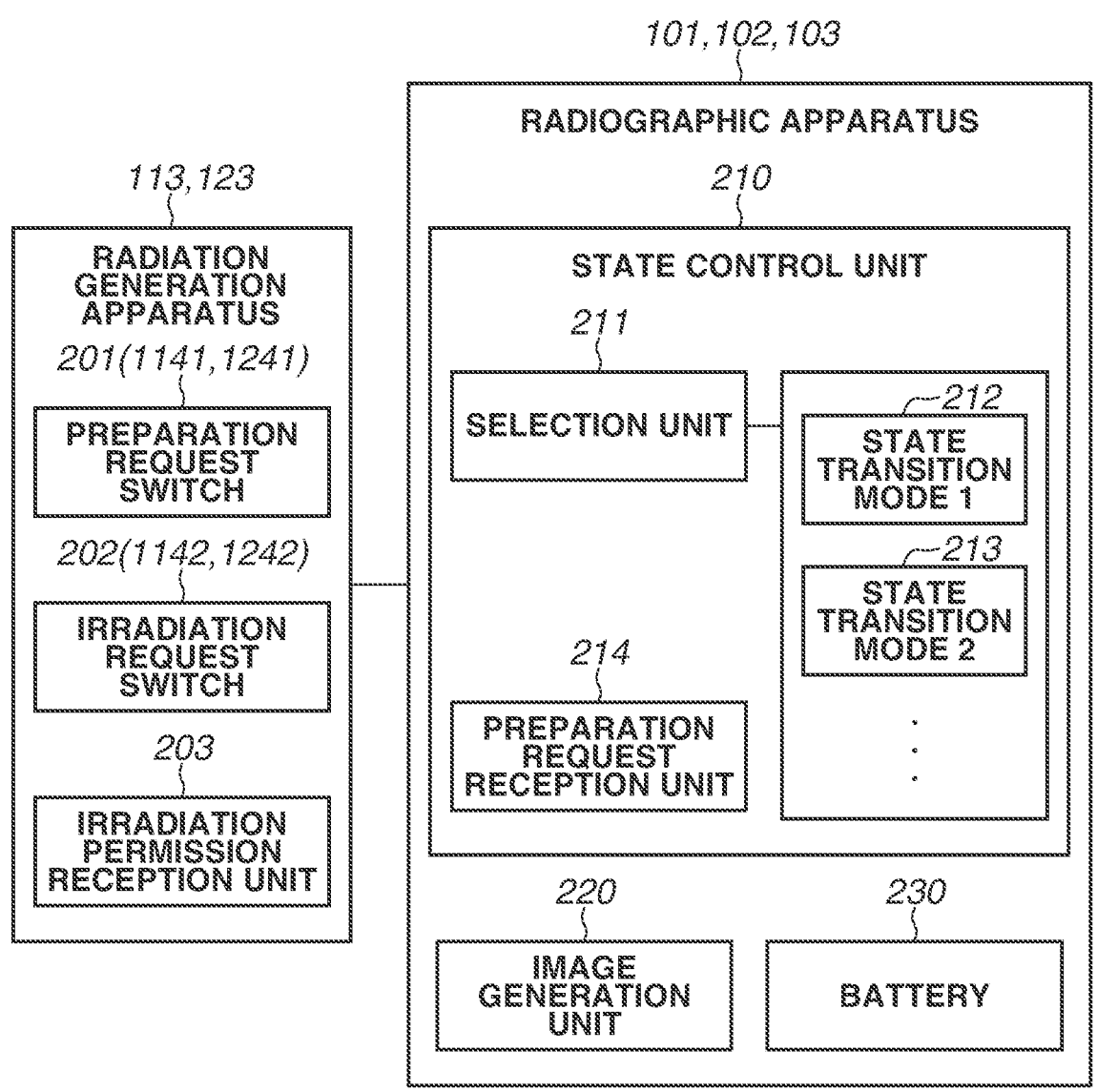
FIG. 2 is a diagram illustrating examples of internal functional configurations of radiation generation apparatuses and radiographic apparatuses illustrated in FIG. 1.

FIG. 2 is a diagram illustrating examples of internal functional configurations of the radiation generation apparatuses 113 and 123 and the radiographic apparatuses 101, 102, and 103 illustrated in FIG. 1 according to the first exemplary embodiment of the present invention.

As illustrated in FIG. 2, each of the radiation generation apparatuses 113 and 123 includes a preparation request switch 201, an irradiation request switch 202, and an irradiation permission reception unit 203. The preparation request switch 201 corresponds to each of the preparation request switches 1141 and 1241 illustrated in FIG. 1, and the irradiation request switch 202 corresponds to each of the irradiation request switches 1142 and 1242 illustrated in FIG. 1.

The radiation generation apparatus 113 transmits information on a preparation start request to one or both of the radiographic apparatuses 101 and 102, and the radiation generation apparatus 123 transmits information on a preparation start request to the radiographic apparatus 103, in response to a press of the preparation request switch 201. Further, the radiation generation apparatus 113 transmits information on an irradiation request to one or both of the radiographic apparatuses 101 and 102, and the radiation generation apparatus 123 transmits information on an irradiation request to the radiographic apparatus 103, in response to a press of the irradiation request switch 202. Each of the radiation generation apparatuses 113 and 123 emits a radiation when the irradiation permission reception unit 203 receives information on radiation irradiation permission in a radiation irradiation-enabled state.

As illustrated in FIG. 2, each of the radiographic apparatuses 101, 102, and 103 includes a state control unit 210 and an image generation unit 220. In each of the radiographic apparatuses 101, 102, and 103, the state control unit 210 switches between a standby state less in power consumption than a radiography-enabled state and the radiography-enabled state. As illustrated in FIG. 2, the state control unit 210 includes a selection unit 211, a first state transition mode 212 (state transition mode 1 in FIG. 2), a second state transition mode 213 (state transition mode 2 in FIG. 2), and a preparation request reception unit 214 that receives a radiation preparation request.

The preparation request reception unit 214 is a reception unit that receives information on a radiation preparation request (information including radiation irradiation preparation start information) from the corresponding radiation generation apparatus 113 or 123. The first state transition mode 212 is a state transition mode causing the radiographic apparatus to make a transition from a first standby state described below selected from a plurality of standby states to the radiography-enabled state. The second state transition mode 213 is a state transition mode causing the radiographic apparatus to make a transition from a second standby state described below selected from the plurality of standby states to the radiography-enabled state.

The selection unit 211 is a selection unit that selects one of the first state transition mode 212 and the second state transition mode 213. The selection unit 211 selects the state transition mode based on state transition characteristics when the corresponding radiographic apparatus 101, 102, or 103 makes a transition from the standby state to the radiography-enabled state and radiation irradiation characteristics when the corresponding radiation generation apparatus 113 or 123 makes a transition to the radiation irradiation-enabled state. The above-described state transition characteristics are characteristics including a transition time for transition from the standby state to the radiography-enabled state. The above-described radiation irradiation characteristics are characteristics including an irradiation preparation time for transition from the standby state to the radiation irradiation-enabled state. At this time, in the present exemplary embodiment, a time necessary for irradiation preparation of each of the radiation generation apparatuses 113 and 123 is referred to as the irradiation preparation time. The irradiation preparation time includes a time until a rotation state of a rotary anode is stabilized and in-plane distribution of the radiation becomes uniform, and thus the irradiation preparation time varies depending on a radiation tube of each of the radiation generation apparatuses 113 and 123. The irradiation preparation time of the radiation generation apparatus 123 on the side of the instrument carriage 120 is often longer than the irradiation preparation time of the radiation generation apparatus 113 on the side of the radiography room 110. If the irradiation request switch 202 is pressed during the irradiation preparation time, for example, the irradiation request is not issued, and is issued when the irradiation preparation time elapses. The preparation request switch 201 and the irradiation request switch 202 often constitute an integrated two-step switch. Further, in the present exemplary embodiment, a time when each of the radiographic apparatuses 101, 102, and 103 makes a transition from the standby state to the radiography-enabled state is referred to as a transition time. The transition time includes a time from when power is supplied to a sensor (sensor 310 in FIG. 3 described below) to when charge accumulation characteristics are stabilized and an artifact disappears. Thus, each of the radiographic apparatuses 101, 102, and 103 is not transitioned to the radiography-enabled state immediately after canceling the standby state, and needs a predetermined time for the transition. In the present exemplary embodiment, the selection unit 211 selects the first state transition mode 212 in a case where the irradiation preparation time is longer than the transition time, and selects the second state transition mode 213 in a case where the irradiation preparation time is shorter than the transition time. Since definitions of the standby state and the radiography-enabled state are different depending on the state transition mode, the transition time is also different.

A case where three types of state transition modes are available is described below. In the present exemplary embodiment, the above-described radiation irradiation characteristics are characteristics calculated by using, for example, the radiation irradiation preparation start information in each of the radiation generation apparatus 113 or 123, and radiation irradiation preparation completion information in each of the radiation generation apparatuses 113 and 123.

The image generation unit 220 generates a radiographic image based on an incident radiation.

A battery 230 is an internal power supply unit that allows the corresponding radiographic apparatus 101, 102, or 103 to operate without an external power supply.

Figure 3:
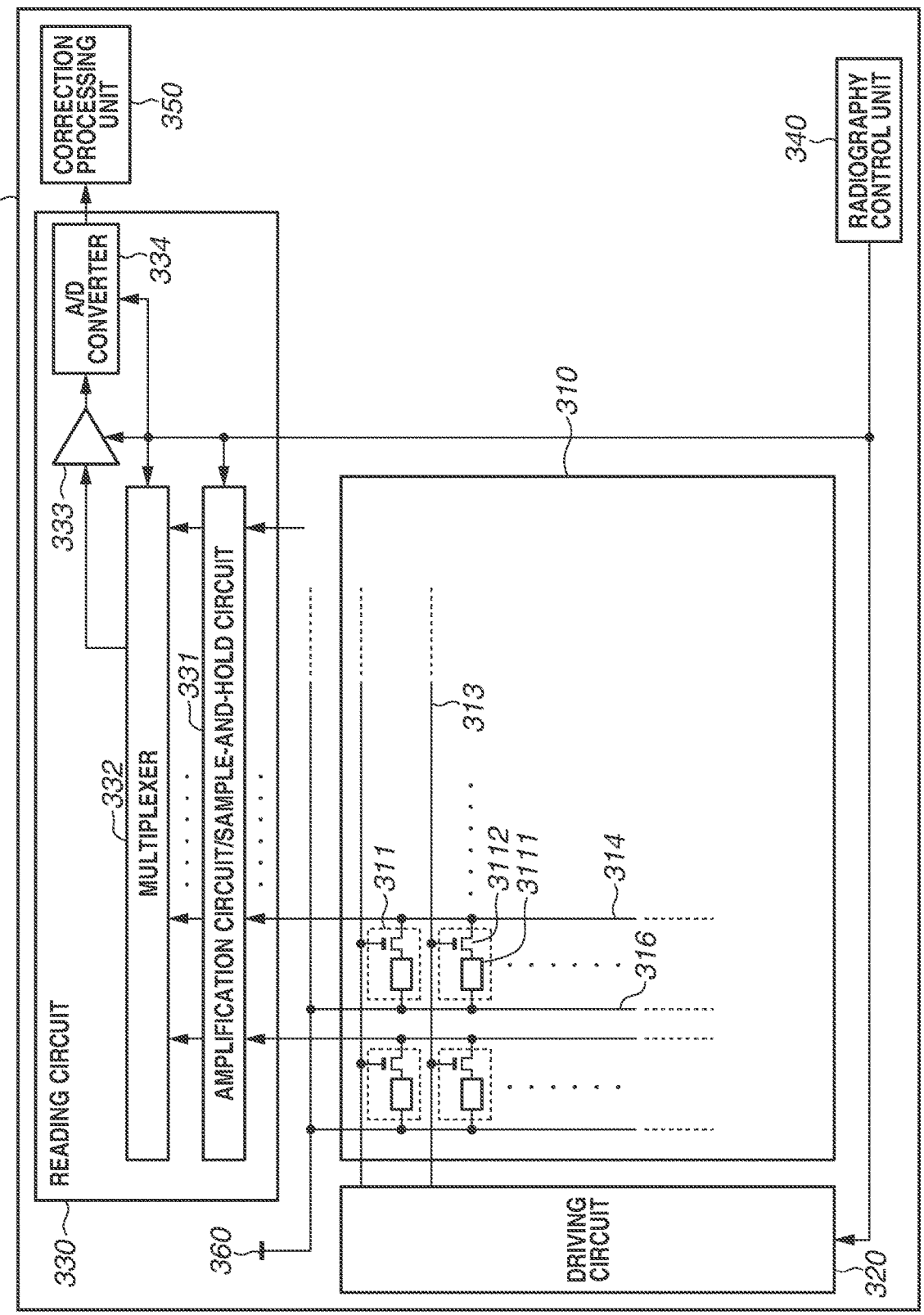
FIG. 3 is a diagram illustrating an example of an internal configuration of an image generation unit illustrated in FIG. 2.

FIG. 3 is a diagram illustrating an example of an internal configuration of the image generation unit 220 illustrated in FIG. 2 according to the first exemplary embodiment of the present invention. As illustrated in FIG. 3, the image generation unit 220 includes the sensor 310, a driving circuit 320, a reading circuit 330, a radiography control unit 340, a correction processing unit 350, and a power supply unit 360.

The sensor 310 includes a plurality of pixels 311 that is arranged in a two-dimensional array so as to form a plurality of rows and a plurality of columns Each of the plurality of pixels 311 includes a conversion device 3111 and a switch device 3112. The conversion device 3111 converts an incident radiation into a charge as an electric signal, and stores the charge. The conversion device 3111 may include a scintillator that converts the radiation into visible light, and a photoelectric conversion device that converts the visible light into a charge, or may be a device that directly converts the radiation into a charge. The switch device 3112 transfers the charge stored in the conversion device 3111 to a corresponding signal line 314. The switch device 3112 includes a transistor such as a thin-film transistor (TFT). The switch device 3112 also includes a control terminal. The switch device 3112 is turned on, i.e., put into a conductive state, in response to supply of an on-state voltage to the control terminal, and is turned off, i.e., put into a nonconductive state, in response to supply of an off-state voltage to the control terminal. A bias voltage is supplied from the power supply unit 360 to one of terminals of the conversion device 3111 via a corresponding bias line 316. The other of the terminals of the conversion device 3111 is connected to the corresponding signal line 314 via the switch device 3112. The control terminal of the switch device 3112 is connected to a corresponding driving line 313. In the sensor 310, a plurality of driving lines 313 each extending in a row direction (lateral direction in FIG. 3) is arranged in a column direction (vertical direction in FIG. 3). Control terminals of switch devices 3112 of the pixels 311 included in the same row are connected to each of the driving lines 313. In the sensor 310, a plurality of signal lines 314 each extending in the column direction is arranged in the row direction. Ones of main terminals of the switch devices 3112 of the pixels 311 included in the same column are connected to each of the signal lines 314.

The driving circuit 320 drives the sensor 310 based on a control signal supplied from the radiography control unit 340. More specifically, the driving circuit 320 supplies driving signals to the control terminals of the respective switch devices 3112 via the driving lines 313. The driving circuit 320 turns on the switch devices 3112 by setting the driving signals to on-state voltages, and turns off the switch devices 3112 by setting the driving signals to off-state voltages. When the switch devices 3112 are turned on, the charges accumulated in conversion devices 3111 are transferred to the signal lines 314.

The reading circuit 330 reads the charge from the sensor 310 based on a control signal supplied from the radiography control unit 340, and generates a signal corresponding to the charge. Then, the reading circuit 330 supplies the generated signal to the correction processing unit 350. As illustrated in FIG. 3, the reading circuit 330 includes a sample-and-hold circuit 331, a multiplexer 332, an amplifier 333, and an analog-to-digital (A/D) converter 334. The sample-and-hold circuit 331 holds the charge read from the conversion devices 3111 for each pixel row. The multiplexer 332 sequentially takes out the charge of the pixels in one row held in the sample-and-hold circuit 331, and supplies the charge to the amplifier 333. The amplifier 333 amplifies the charge supplied from the multiplexer 332, and supplies the amplified charge to the A/D converter 334. The A/D converter 334 converts an analog signal supplied from the amplifier 333 into a digital signal (corresponding to data on the above-described radiographic image), and supplies the digital signal to the correction processing unit 350. The correction processing unit 350 performs dark correction in which data on a dark image acquired from only a dark charge component without emitting a radiation is subtracted from the data on the radiographic image converted into digital values, thereby acquiring a captured image from which the unnecessary dark charge component is removed. The power supply unit 360 supplies main operation voltages such as the bias voltage, and can operate by an external power supply or a power supply from the battery 230.

Figure 4:
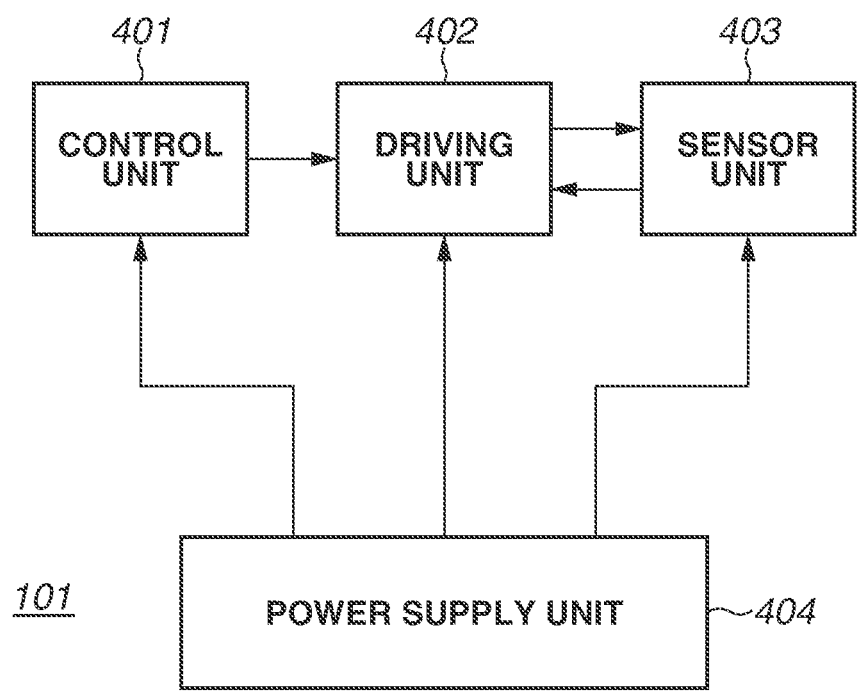
FIG. 4 is a diagram illustrating an example of an internal functional configuration of one of the radiographic apparatuses.

Three state transition modes different in definitions of the standby state and the radiography-enabled state are described with reference to FIG. 4 and FIGS. 5A and 5B. FIG. 4 is a conceptual diagram illustrating functional blocks into which the configuration of each of the radiographic apparatuses described in FIG. 2 and FIG. 3 is divided by power control types. The radiographic apparatus 101 is described below as a representative example.

An electric internal configuration of the radiographic apparatus 101 can be roughly classified into a control unit 401, a driving unit 402, a sensor unit 403, and a power supply unit 404. The sensor unit 403 that generates a radiographic image based on an incident radiation includes the sensor 310, the driving circuit 320, and the reading circuit 330 of the image generation unit 220 illustrated in FIG. 3. The driving unit 402 includes part of the radiography control unit 340 of the image generation unit 220 illustrated in FIG. 3, and may include a programmable logic circuit such as a field programmable gate array (FPGA) and a complex programmable logic device (CPLD). Further, the driving unit 402 performs operation control such as driving and reading of the sensor unit 403. The control unit 401 includes the state control unit 210 illustrated in FIG. 2, the correction processing unit 350 illustrated in FIG. 3, and part of the radiography control unit 340, and performs control of the driving unit 402, communication with outside, and the like. The control unit 401 includes a central processing unit (CPU), and memories such as a flash memory and a dynamic random access memory (DRAM), and a wired/wireless communication interface that are peripheral circuits of the CPU. The power supply unit 404 can individually supply power to the control unit 401, the driving unit 402, and the sensor unit 403.

Operation to make a transition to the standby state and the radiography-enabled state in the state transition mode 1 is described with reference to FIG. 5A. In this case, description is given assuming that the power supply unit 404 is operating even though the power supply unit 404 is not illustrated because the description relates to a state where the power is on. In the state transition mode 1 illustrated in FIG. 5A, in the standby state (first standby state), the power supply unit 404 does not supply power to the sensor unit 403 and the driving unit 402, but supplies power to the control unit 401. Thus, in the standby state of the state transition mode 1, the radiographic apparatus 101 operates so that the sensor unit 403 and the driving unit 402 do not operate but the control unit 401 operates. Then, the power supply unit 404 starts to supply power to the driving unit 402 with a press of the preparation request switch 201 as a trigger, and the driving unit 402 accordingly starts to operate. In a case where the driving unit 402 includes the FPGA, the driving unit 402 starts to operate by performing configuration and then performing initialization after receiving a power supply. The power supply unit 404 supplies power to the sensor unit 403. The sensor unit 403 performs preparation driving during a period until the charge accumulation characteristics of the sensor 310 are stabilized and an artifact is smaller than a certain value. The driving unit 402 controls the sensor unit 403 to perform the preparation driving, and the sensor unit 403 performs the preparation driving under the control of the driving unit 402. In the case of the state transition mode 1, a transition time (first transition time) T1 to the radiography-enabled state is a time from when the driving unit 402 is turned on to when the preparation driving of the sensor unit 403 is completed.

Operation to make a transition to the standby state and the radiography-enabled state in the state transition mode 2 is described with reference to FIG. 5B. In the state transition mode 2 illustrated in FIG. 5B, in the standby state (second standby state), the power supply unit 404 does not supply power to the sensor unit 403, but supplies power to the driving unit 402 and the control unit 401. Thus, in the standby state of the state transition mode 2, the control unit 401 and the driving unit 402 are operating. Then, the power supply unit 404 starts to supply power to the sensor unit 403 with a press of the preparation request switch 201 as a trigger. The driving unit 402 controls the sensor unit 403 to perform preparation driving, and the sensor unit 403 performs the preparation driving under the control of the driving unit 402. In the case of the state transition mode 2, a transition time (second transition time) T2 to the radiography-enabled state is a time from when the sensor unit 403 is turned on to when the preparation driving of the sensor unit 403 is completed. The transition time T2 to the radiography-enabled state is shorter than the transition time T1 to the radiography-enabled state because the time for setting such as the configuration and for preparation after the driving unit 402 is turned on is not present. Thus lengths of the transition time to the radiography-enabled state between the two state transition modes have a relationship of T1>T2.

Although not described with reference to the drawings, in a state transition mode 3, the power supply unit 404 supplies power to the control unit 401, the driving unit 402, and the sensor unit 403 in the standby state (third standby state), so that the preparation driving of the sensor unit 403 is also performed. Thus, the preparation driving is not started with a press of the preparation request switch 201 as a trigger, but the state can be transitioned to the radiography-enabled state with the press of the preparation request switch 201. In the standby state of the state transition mode 3, the amplifier 333 and the A/D converter 334 of the reading circuit 330 of the sensor unit 403 operate with low power consumption, which makes it possible to reduce the power consumption as compared with the radiography-enabled state.

In the radiographic apparatus 101 that operates not by an external power supply but by a power supply from the battery 230, it is desirable to reduce the power consumption to extend an available time. Taking into consideration an actual radiography operation cycle, the total time in the standby state is overwhelmingly longer than the total time in the radiography-enabled state. Thus, reduction of the power consumption in the standby state is effective to extending of the available time. FIG. 6 illustrates a relationship between each of the state transition modes and the power consumption in the standby state. As illustrated in FIG. 6, the power consumption in the standby state is larger as the number of units receiving power from the power supply unit 404 in the standby state is increased, and the power consumption in the standby state becomes larger in order of the state transition mode 1, the state transition mode 2, and the state transition mode 3. In contrast, the transition time to the radiography-enabled state is shorter as the number of units receiving power from the power supply unit 404 in the standby state is increased, and the transition time becomes longer in order of the state transition mode 3, the state transition mode 2, and the state transition mode 1. In other words, the transition time to the radiography-enabled state is longer as the power consumption in the standby state is smaller.

For example, in a case where the preparation request switch 1141 and the irradiation request switch 1142 illustrated in FIG. 1 are simultaneously pressed, the radiation generation apparatus 113 notifies the radiographic apparatus 101 of generation of a radiation preparation request. Further, the radiation generation apparatus 113 makes a transition to the radiation irradiation-enabled state in response to a press of the preparation request switch 1141, and transmits a radiation irradiation request to the radiographic apparatus 101. When the preparation request reception unit 214 receives the radiation preparation request from the radiation generation apparatus 113, the radiographic apparatus 101 cancels the standby state and makes a transition to the radiography-enabled state. In a case where the time T1 from reception of the radiation preparation request to transition to the radiography-enabled state is longer than the transition time to the radiation irradiation-enabled state, the radiation irradiation request is already received at the time when the state is transitioned to the radiography-enabled state. Thus, when the radiographic apparatus 101 transmits irradiation permission and the radiation generation apparatus 113 performs irradiation, the radiography-enabled state of the radiographic apparatus 101 is a bottleneck for an irradiation delay 501 from a press of the irradiation request switch 1142 to the radiation irradiation. In this example, the case where the preparation request switch 1141 and the irradiation request switch 1142 are simultaneously pressed has been described; however, operation is similar in a case where the transition to the radiography-enabled state is put on hold in a state where the preparation request switch 1141 is pressed. In other words, the radiography-enabled state of the radiographic apparatus 101 is a bottleneck for the time from a press of the preparation request switch 1141 to completion of preparation of the radiation generation apparatus 113 and the radiographic apparatus 101 (system preparation delay). Thus, the selection unit 211 of the state control unit 210 selects the state transition mode through a procedure illustrated in FIG. 7.

First, in step S701, the selection unit 211 acquires an irradiation preparation time Tx of the radiation generation apparatus. The irradiation preparation time Tx is different between the radiation generation apparatuses 113 and 123. As a method of acquiring the irradiation preparation time Tx, there is a method of previously setting a time necessary for irradiation preparation of the radiation generation apparatus to the radiographic apparatus. The irradiation preparation time can be acquired from a specification value and a design value of the radiation generation apparatus, and an engineer can set the irradiation preparation time when the radiographic apparatus is installed. Alternatively, the radiographic apparatus may acquire the irradiation preparation time by communicating with the radiation generation apparatus. Yet alternatively, a console or another device may acquire the irradiation preparation time by communicating with the radiation generation apparatus, and the device having acquired information on the irradiation preparation time may notify the radiographic apparatus of the irradiation preparation time. The irradiation preparation time Tx may be acquired from the radiation generation apparatus, or may be obtained by actually emitting a radiation in a state where no object is placed and measuring an irradiation preparation time. The irradiation preparation time may slightly vary even when the irradiation is performed under the same condition, and the irradiation preparation time may vary when an irradiation condition such as a tube voltage is changed. Thus, the irradiation preparation time may be defined by taking an average value, the minimum value, the maximum value, or the like, or may be set as a value varied depending on the irradiation condition. Still yet alternatively, the information on the irradiation preparation time may be acquired every time the radiographic apparatus is activated or initialized, or may be acquired in a case where the radiation generation apparatus is changed or the irradiation condition is changed. Further, the information on the irradiation preparation time may be held and managed as a parameter by the radiographic apparatus, the console, or the other device in association with a type, an individual difference, a radiographic procedure, or an irradiation condition of the radiation generation apparatus.

A specific example of a method for the radiographic apparatus 101 to acquire the irradiation preparation time necessary for the irradiation preparation of the radiation generation apparatus 113 is described. In response to a simultaneous press of the preparation request switch 1141 and the irradiation request switch 1142 of the radiation generation apparatus 113, the radiation generation apparatus 113 notifies the radiographic apparatus 101 of generation of the radiation preparation request. The radiographic apparatus 101 operates a timer to measure an elapsed time from when the radiation preparation request is received. When the radiation generation apparatus 113 is transitioned to the radiation irradiation-enabled state, the radiation generation apparatus 113 notifies the radiographic apparatus 101 of the radiation irradiation request. When receiving the radiation irradiation request, the radiographic apparatus 101 checks the timer to measure the time from when the radiation preparation request is received. The radiographic apparatus 101 can acquire the irradiation preparation time from the measurement. In this method, the irradiation preparation time can be measured when the radiographic apparatus 101 is installed. In this example, the case has been described where the preparation request switch 1141 and the irradiation request switch 1142 are simultaneously pressed; however, the method is not limited to the case. The method is also applicable to a case where the preparation request switch 1141 and the irradiation request switch 1142 are pressed with a time difference within the irradiation preparation time. In place of reception of the radiation irradiation request, the radiographic apparatus 101 may detect a start of radiation irradiation by using a method for automatically detecting radiation irradiation. The radiographic apparatus 101 can acquire the irradiation preparation time by checking the timer in response to detection of the radiation irradiation and measuring the time from when the radiation preparation request is received.

Next, in step S702, the selection unit 211 compares the acquired irradiation preparation time Tx with the transition time T1 to the radiography-enabled state in the state transition mode 1. In a case where the irradiation preparation time Tx≥the transition time T1 is established (YES in step S702), the state transition mode 1 is selected in step S703. In a case where the irradiation preparation time Tx≤the transition time T1 is established (NO in step S702), the processing proceeds to step S704. In step S704, the selection unit 211 compares the acquired irradiation preparation time Tx with the transition time T2 to the radiography-enabled state in the state transition mode 2. In a case where the irradiation preparation time Tx≥the transition time T2 is established (YES in step S704), the state transition mode 2 is selected in step S705. In a case where the irradiation preparation time Tx≤the transition time T2 is established (NO in step S704), the state transition mode 3 is selected in step S706.

Figure 7:
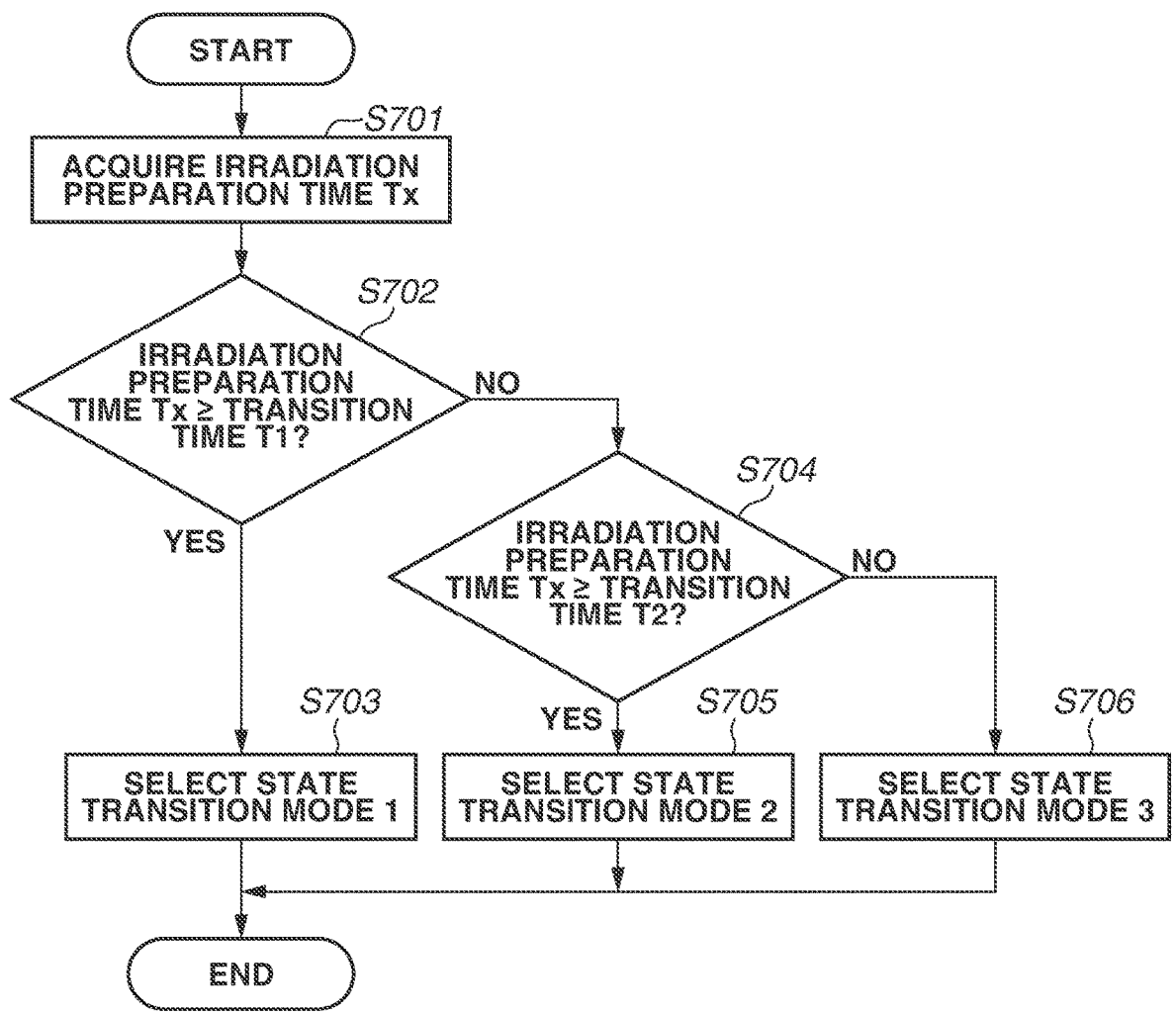
FIG. 7 is a flowchart illustrating an example of a processing procedure according to a first exemplary embodiment.
Figure 8:
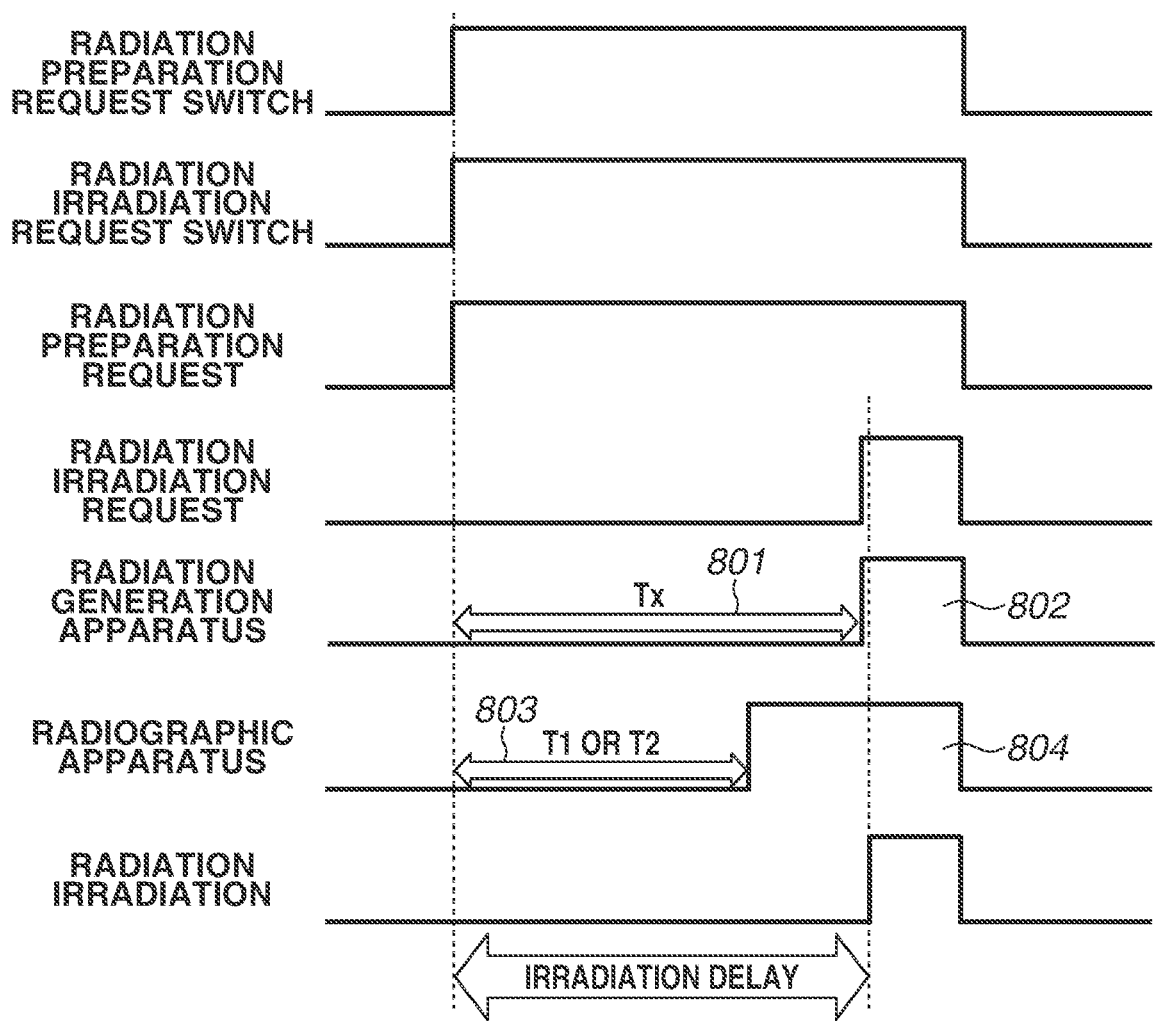
FIG. 8 is a conceptual diagram illustrating operation of a radiographic apparatus according to the first exemplary embodiment.

The operation in the case where the state transition mode 1 or 2 is selected by the procedure illustrated in FIG. 7 is described with reference to FIG. 8. In the case where the preparation request switch 1141 and the irradiation request switch 1142 are simultaneously pressed, the radiation generation apparatus 113 notifies the radiographic apparatus 101 of generation of the radiation preparation request. Further, in response to a press of the preparation request switch 1141, the radiation generation apparatus 113 makes a transition to the radiation irradiation-enabled state (802) after the radiation irradiation preparation time Tx (801), and transmits the radiation irradiation request to the radiographic apparatus 101. When the preparation request reception unit 214 receives the radiation preparation request from the radiation generation apparatus 113, the radiographic apparatus 101 cancels the standby state and makes a transition to the radiography-enabled state (804) after the transition time T1 or T2 (803). At this time, since the irradiation preparation time Tx ≥the transition time T1 or T2 is established, the radiographic apparatus 101 has already made a transition to the radiography-enabled state at a time when the radiographic apparatus 101 receives the radiation irradiation request from the radiation generation apparatus 113. Thus, when the radiographic apparatus 101 transmits irradiation permission and the radiation generation apparatus 113 performs irradiation, the irradiation delay from a press of the irradiation request switch 1142 to the radiation irradiation is determined by the irradiation preparation time Tx of the radiation generation apparatus 113.

Figure 9:
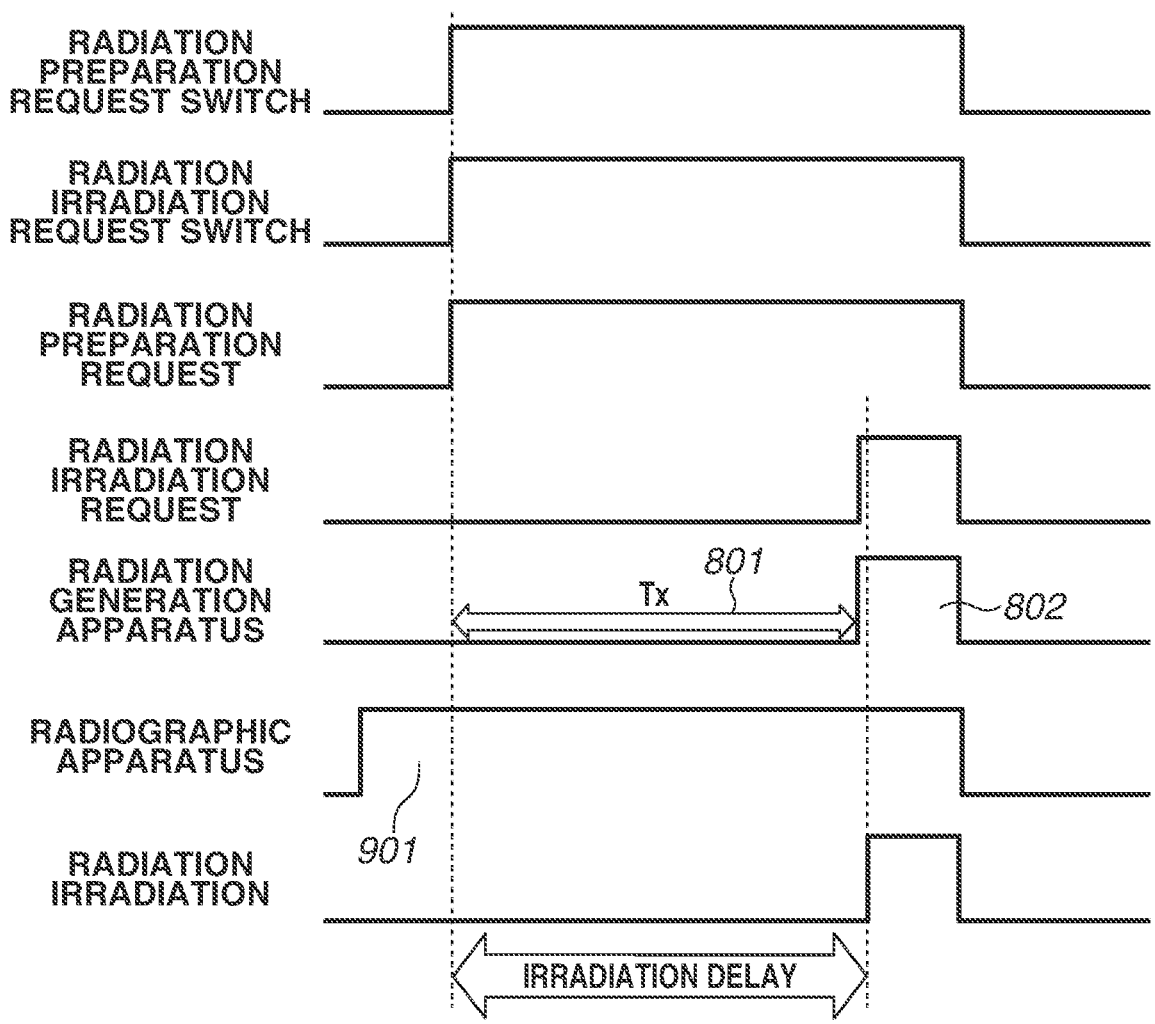
FIG. 9 is a conceptual diagram illustrating the operation of the radiographic apparatus according to the first exemplary embodiment.

The operation in a case where the state transition mode 3 is selected by the procedure illustrated in FIG. 7 is described with reference to FIG. 9. In the case of the state transition mode 3, the radiographic apparatus 101 makes a transition to the radiography-enabled state (901) before receiving the radiation preparation request from the radiation generation apparatus 113. For example, a timing when the radiographic apparatus 101 is turned on may be used as a trigger for the transition, or a physical switch for the transition may be provided. An instruction to cancel the standby state may be transmitted by operation on the console, or the standby state may be canceled in response to operation to select a radiography order. Operation of the radiation generation apparatus 113 after the preparation request switch 1141 of the radiation generation apparatus 113 is pressed is similar to the operation thereof in the state transition mode 1 or 2. Since the radiographic apparatus 101 has already made a transition to the radiography-enabled state, the irradiation delay is determined by the irradiation preparation time Tx of the radiation generation apparatus 113. Thus, the irradiation delay is a constant time determined by the irradiation preparation time Tx whichever mode is selected from among the state transition modes 1 to 3.

As described above, in the present exemplary embodiment, the selection unit 211 selects the standby state from the plurality of standby states so that the transition time for the radiographic apparatus 101 to make a transition from the standby state to the radiography-enabled state is shorter than the irradiation preparation time Tx. As a result, in the case where the radiographic apparatus has a plurality of standby state canceling methods, a mechanism to select the optimum standby state canceling method in terms of power consumption can be provided.

In the present exemplary embodiment, the example in which three state transition modes are available has been described; however, the number of modes in the present invention is not limited thereto as long as the mode is selectable from a plurality of state transition modes. The state transition mode 1 is set to the state where the control unit 401 (CPU) operates. Alternatively, for example, a microcomputer specialized in lower power consumption may be adopted, and the state transition mode 1 may be set to a state where communication with an external device such as the console is minimally performable. The sensor unit 403 may be turned on at the same time as or prior to when the driving unit 402 is turned on, or may be turned on before the preparation request switch 1141 is pressed within a range not adversely affecting image quality.

Figure 10:
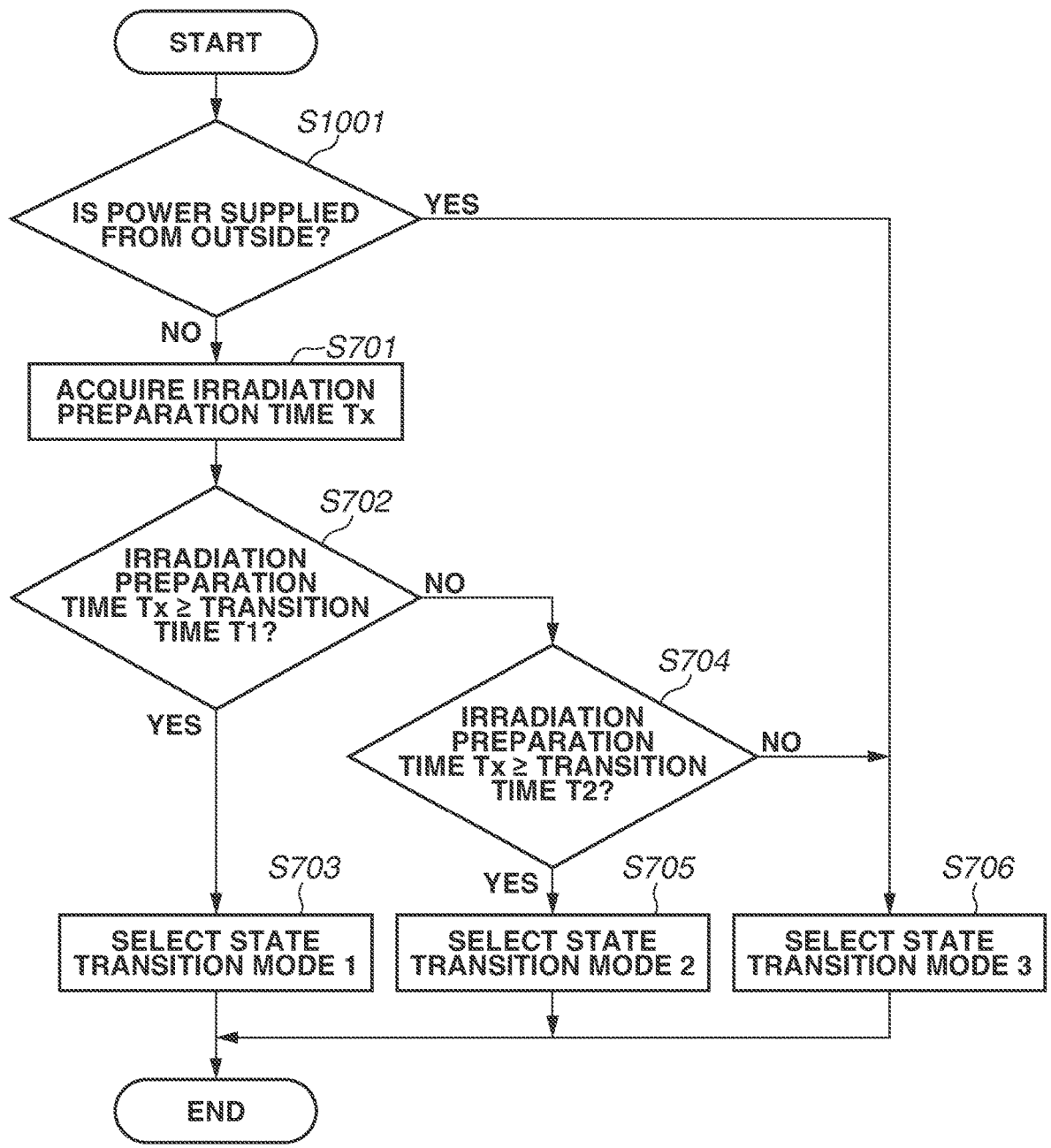
FIG. 10 is a flowchart illustrating an example of a processing procedure according to a second exemplary embodiment.

A second exemplary embodiment is described with reference to FIG. 10. FIG. 10 illustrates a procedure for selecting a state transition mode according to the second exemplary embodiment. The second exemplary embodiment is different from the first exemplary embodiment illustrated in FIG. 7 in the method of determining the state transition mode.

In the procedure according to the second exemplary embodiment illustrated in FIG. 10, in step S1001 before the procedure according to the first exemplary embodiment illustrated in FIG. 7, it is determined whether the radiographic apparatus 101 receives a power supply not from the battery but from outside. In a case where the radiographic apparatus 101 does not receive the power supply from outside (NO in step S1001), the processing proceeds to step S701, and a procedure similar to the procedure according to the first exemplary embodiment is performed. In a case where the radiographic apparatus 101 receives the power supply from outside (YES in step S1001), the processing proceeds to step S706, and the state transition mode 3 is selected. The noise in the radiographic image is reduced as duration of the radiography-enabled state is longer. Thus, in a state where power is supplied from outside, priority is given to image quality rather than reduction of power consumption. Thus, in the case where power is supplied from outside, control to select the state transition mode 3 is enabled. Processing in other steps is similar to the processing according to the first exemplary embodiment. Thus, detailed description of the processing is omitted.

A third exemplary embodiment is described with reference to FIG. 11 and FIG. 12. In a case where the radiographic apparatus 101 is installed in a hospital, a medical examination car, or the like, the irradiation preparation time of a radiation generation apparatus that may be used therewith is previously stored in association with identification information specifying the radiation generation apparatus. The radiographic apparatus 101 is used in an instrument carriage as necessary in addition to a general radiography room. In such a case, the irradiation preparation time in each case is stored in association with the identification information on the radiation generation apparatus. Alternatively, since the irradiation condition is changed depending on a radiography procedure in addition to the information on the radiation generation apparatus, the irradiation preparation time varies. Thus, the irradiation preparation time may be stored in association with the radiation generation apparatus and information on the procedure. Further, the irradiation preparation time may be stored not in the radiographic apparatus 101 but in the console or the like that controls the radiographic apparatus 101. The method of acquiring the irradiation preparation time of the radiation generation apparatus is similar to the method in the first and second exemplary embodiments described above.

In a case where the state transition mode suitable for each of the radiation generation apparatuses is defined as illustrated in FIG. 11, the state control unit 210 stores the state transition mode suitable for each of the radiation generation apparatuses so that the transition time to the radiography-enabled state is less than or equal to the irradiation preparation time. The radiation generation apparatus used in the general radiography room is typically shorter in irradiation preparation time than the radiation generation apparatus mounted on the instrument carriage. Thus, the suitable state transition mode may be different in some cases.

A procedure for selecting a state transition mode according to the third exemplary embodiment is described with reference to FIG. 12. In step S1201, the radiographic apparatus 101 acquires information on the radiation generation apparatus to be used, in a state where the information illustrated in FIG. 11 is stored. The information may be transmitted from the radiation generation apparatus to be used to the radiographic apparatus 101, or the console or the like may receive the information and transmit the information to the radiographic apparatus 101. Next, in step S1202, the received information is compared with the information in FIG. 11. In a case where the received information is coincident with information on a general radiography room A (YES in step S1202), the state transition mode 1 suitable for the general radiography room A is selected in step S1203. In a case where the received information is not coincident with the information on the general radiography room A (NO in step S1202), the processing proceeds to step S1204. In a case where the received information is coincident with information on a general radiography room B (YES in step S1204), the state transition mode 2 is selected in step S1205. In a case where the received information is not coincident with the information on the general radiography room B but is coincident with information on the instrument carriage, or the received information is undefined information (NO in step S1204), the state transition mode 3 is selected in step S1206. The subsequent operation is similar to the operation in the first or second exemplary embodiment. Retention of the information illustrated in FIG. 11 and a determination illustrated in FIG. 12 may be performed not by the radiographic apparatus but by the console or the like.

The present invention can be realized by supplying a program that implements one or more functions of the above-described exemplary embodiments to a system or an apparatus via a network or a storage medium, and causing one or more processors of a computer in the system or the apparatus to read and execute the program. Further, the present invention can be realized by a circuit (e.g., application specific integrated circuit (ASIC)) that implements one or more functions.

The program and a computer-readable storage medium storing the program are included in the present invention.

The above-described exemplary embodiments of the present invention are merely examples of embodiments for implementing the present invention, and the technical scope of the present invention must not be limited thereby. In other words, the present invention can be implemented in various forms without departing from the technical idea or the major characteristics of the present invention.

According to the exemplary embodiments of the present invention, in the case where the radiographic apparatus has the plurality of standby state canceling methods, an optimum standby state canceling method in terms of power consumption can be selected.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A radiographic apparatus configured to capture a radiographic image based on an incident radiation, the radiographic apparatus operating in any of a plurality of standby states different in power consumption, each of the standby states being less in power consumption than a radiography-enabled state where the radiographic apparatus is enabled to capture the radiographic image, the radiography apparatus comprising:

a selection unit configured to select a standby state from the plurality of standby states so that a transition time is shorter than an irradiation preparation time, the transition time being a time necessary for the radiographic apparatus to make a transition from the standby state to the radiography-enabled state after a radiation irradiation preparation request is received, the irradiation preparation time being a time necessary for a radiation generation apparatus configured to generate a radiation to prepare irradiation of the radiation after the radiation irradiation preparation request is received.

2. The radiographic apparatus according to claim 1,
wherein the plurality of standby states includes a first standby state and a second standby state greater in power consumption than the first standby state, and
wherein, in a case where a first transition time for transition from the first standby state to the radiography-enabled state is longer than the irradiation preparation time, the selection unit selects the second standby state from the plurality of standby states.

3. The radiographic apparatus according to claim 2,
wherein the plurality of standby states further includes a third standby state greater in power consumption than the second standby state, and
wherein, in a case where a second transition time for transition from the second standby state to the radiography-enabled state is longer than the irradiation preparation time, the selection unit selects the third standby state from the plurality of standby states.

4. The radiographic apparatus according to claim 3, further comprising:
a sensor unit configured to generate the radiographic image;
a driving unit configured to perform operation control of the sensor unit;
a control unit configured to control the driving unit; and
a power supply unit configured to individually supply power to the sensor unit, the driving unit, and the control unit.

5. The radiographic apparatus according to claim 4,
wherein, in the first standby state, the power supply unit does not supply power to the sensor unit and the driving unit, but supplies power to the control unit, and
wherein, in the second standby state, the power supply unit does not supply power to the sensor unit, but supplies power to the driving unit and the control unit.

6. The radiographic apparatus according to claim 4, wherein in the first standby state, power consumption is reduced by not supplying power to at least one of the sensor unit, the driving unit and the control unit.

7. The radiographic apparatus according to claim 1, further comprising a reception unit configured to receive the radiation irradiation preparation request,
wherein the radiographic apparatus makes a transition from the standby state to the radiography-enabled state with reception of the radiation irradiation preparation request as a trigger.

8. The radiographic apparatus according to claim 1, further comprising a battery configured to operate the radiographic apparatus without a power supply from outside of the radiographic apparatus.

9. The radiographic apparatus according to claim 8, wherein the selection unit selects the standby state from the plurality of standby states based on a determination on whether the radiographic apparatus receives power from not the battery but the outside.

10. The radiographic apparatus according to claim 1, wherein, in a case where a piece of identification information specifying, among a plurality of radiation generation apparatuses, a radiation generation apparatus to be used as the radiation generation apparatus is acquired, the selection unit selects a standby state stored in association with the acquired piece of identification information from the plurality of standby states previously stored in association with pieces of identification information specifying the plurality of radiation generation apparatuses.

11. A radiographic system, comprising:
the radiographic apparatus according to claim 1; and
the radiation generation apparatus.

12. A method of controlling a radiographic apparatus configured to capture a radiographic image based on an incident radiation, the radiographic apparatus operating in any of a plurality of standby states different in power consumption, each of the standby states being less in power consumption than a radiography-enabled state where the radiographic apparatus is enabled to capture the radiographic image, the method comprising:
selecting a standby state from the plurality of standby states so that a transition time is shorter than an irradiation preparation time, the transition time being a time necessary for the radiographic apparatus to make a transition from the standby state to the radiography-enabled state after a radiation irradiation preparation request is received, the irradiation preparation time being a time necessary for a radiation generation apparatus configured to generate a radiation to prepare irradiation of the radiation after the radiation irradiation preparation request is received.

13. A non-transitory computer-readable storage medium storing a program for causing a computer to execute the method of controlling the radiographic apparatus according to claim 12.

* * * * *